United States Patent [19]

Roby et al.

[11] Patent Number: 5,902,875
[45] Date of Patent: May 11, 1999

[54] POLYESTERAMIDE, ITS PREPARATION AND SURGICAL DEVICES FABRICATED THEREFROM

[75] Inventors: Mark S. Roby, Killingworth; Ying Jiang, North Haven, both of Conn.

[73] Assignee: United States Surgical Corporation, Norwalk, Conn.

[21] Appl. No.: 09/014,801

[22] Filed: Jan. 28, 1998

Related U.S. Application Data

[60] Provisional application No. 60/036,538, Jan. 28, 1997.

[51] Int. Cl.$^6$ .................................................. C08G 69/44
[52] U.S. Cl. ......................... 528/310; 528/170; 528/322; 528/323; 528/327; 528/354; 528/355; 528/361; 525/411; 525/415; 525/417; 606/139; 606/228; 606/230
[58] Field of Search ..................................... 528/310, 322, 528/354, 323, 327, 170, 361, 355; 525/411, 415, 417; 606/139, 228, 230

[56] References Cited

U.S. PATENT DOCUMENTS

| | | | |
|---|---|---|---|
| Re. 30,170 | 12/1979 | Goodman et al. | 528/327 |
| 4,226,243 | 10/1980 | Shalaby | 128/335.5 |
| 4,343,931 | 8/1982 | Barrows | 528/291 |
| 5,349,045 | 9/1994 | Jiang | 528/323 |
| 5,446,108 | 8/1995 | Jiang | 525/417 |
| 5,483,009 | 1/1996 | Jiang | 525/417 |

*Primary Examiner*—P. Hampton-Hightower

[57] ABSTRACT

A polyesteramide suitable for use in the fabrication of absorbable surgical devices such as monofilament and multifilament sutures, films, sheets, plates, clips, staples, pins, screws, and the like, is obtained by reacting a monoalkanolamine such as ethanolamine with a diacid halide such as succinic acidchloride to provide a diamidediol and thereafter reacting the diamidediol with the same or different diacid halide under polymerization conditions to form the polyesteramide.

21 Claims, No Drawings ical Field

An absorbable polyesteramide, its preparation and absorbable surgical devices fabricated therefrom such as monofilament and multifilament sutures, films, sheets, plates, clips, stables, pins, screws, and the like are described herein.

BACKGROUND

Polyesteramides are polymers containing both ester linkages and amide linkages. The significance of the polyesteramides for the technology of surgical devices stems from the fact that the susceptibility of their ester linkages to hydrolysis confers upon these resins the ability to be absorbed, or resorbed, by a body into which they have been implanted and their amide linkages confer upon them the desirable mechanical properties characteristic of the polyamides.

Fiber-forming polyesteramides obtained from the single stage reaction of approximately equimolar amounts of a monoalkanolamine and a dicarboxylic acid are known from U.S. Pat. No. 2,386,454. Polyesteramides indicated to be useful for the manufacture of absorbable sutures and other surgical devices are disclosed in U.S. Pat. No. 4,226,243 as obtained from the reaction of a bis-oxyamidodiol (itself derived from the reaction of diethyl oxalate with a monoalkanolamine such as ethanolamine) with a dicarboxylic acid ester. U.S. Pat. No. 4,343,931 discloses absorbable surgical devices manufactured from polyesteramides obtained by reacting a diamine with lactic acid or glycolic acid to produce a diamidediol, which is then reacted with a bischloroformate or a compound selected from the group consisting of dicarboxylic acids, diacidchlorides and dicarboxylic acid anhydrides.

Nylon refers to a family of high strength, resilient synthetic materials, the long chain molecules of which contain recurring amide groups. Articles fabricated from nylon have been widely accepted for a variety of applications. Certain surgical applications, however, require a surgical device that is bioabsorbable. Nylon is not bioabsorbable and is therefore unacceptable in such circumstances.

It would be desirable to provide a surgical device that has strength and resiliency characteristics equivalent to those of nylon, but which is bioabsorbable.

SUMMARY

A polyesteramide is provided herein which possesses units of the structure

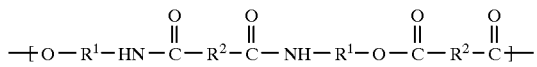

wherein $R^1$ and $R^2$ are divalent groups.

The foregoing polyesteramide is prepared by reacting a monoalkanolamine with a diacid halide to form a diamidediol, the diamidediol then being reacted with diacidchloride to provide the polyesteramide.

The polyesteramide herein can be fabricated into a wide variety of absorbable surgical devices including monofilament and multifilament sutures, films, sheets, plates, clips, staples, pins, screws, and so forth.

DESCRIPTION OF THE PREFERRED EMBODIMENTS

The polyesteramide described herein is obtained by a two-step process the first step of which involves the reaction of a monoalkanolamide of the structure HO—$R^1$—$NH_2$ wherein $R^1$ is a divalent group, e.g., a hydrocarbylene group possessing from 2 to about 20 carbons, and preferably an alkylene group of from 2 to 4 carbon atoms, with a diacid halide of the structure

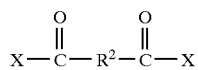

wherein X is X is F, Cl, Fr or I and $R^2$ is a divalent group, e.g., a hydrocarbylene group possessing from 2 to about 20 carbon atoms, and preferably an alkylene group of from 2 to 4 carbon atoms, under conditions tending to promote the formation of an intermediate diamidediol and to exclude or minimize the formation of polymer and/or other undesirable reaction product(s). This reaction is thought to proceed as follows:

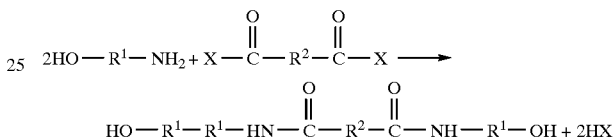

Suitable monoalkanolamines for this reaction include ethanolamine, 3-amino-1-propanol, 4-amino-1-butanol, 5-amino-1-pentanol, 6-amino-1-hexanol, 2-amino-2-methyl-1-propanol, 3-aminomethylcyclohexanemethanol, 4-aminomethylcyclohexanemethanol, 5-amino-2,2-dimethyl-1-pentanol, and the like. Of the foregoing, ethanolamine is preferred.

Suitable diacid halides include those derived from succinic acid, 2,3-dimethylsuccinic acid, glutaric acid, 3,3-dimethylglutaric acid, 3-methyladipic acid, adipic acid, pimelic acid, suberic acid, azelaic acid, sebacic acid, 1,9-nonanedicarboxylic acid, 1,10-decanedicarboxylic acid, 1,11-undecanedicarboxylic acid, 1,12-dodecanedicarboxylic acid, 1,13-tridecanedicarboxylic acid, 1,14-tetradecanedicarboxylic acid, 1,15-pentadecanedicarboxylic acid, 1,16-hexadecanedicarboxylic acid, trans-β-hydromuconic acid, fumaric acid, diglycolic acid, 3,3'-oxydipropionic acid, 4,4'-oxydibutyric acid, 4,5'-oxydivaleric acid, 6,6'-oxydicaproic acid, 8,8'-oxydicaprylic acid, 6-oxaundecanedioic acid, 5-oxaazelaic acid, 5-oxadodecanedioic acid, 5-oxatetradecanedioic acid, 5-oxahexadecanedioic acid, 6-oxadodecanedioic acid, 6-oxatridecanedioic acid, 6-oxapentadecanedioic acid, 6-oxaheptadecanedioic acid, 7-oxapentadecanedioic acid, 10-oxanonadecanedioic acid and other oxa-aliphatic dicarboxylic acids, phthalic acid, isophthalic acid, tetraphthalic acid and other aromatic dicarboxylic acids, 1,2-cyclobutanedicarboxylic acid, and 1,4-cyclohexanedicarboxylic acid. Of these diacid halides, succinic acidchloride is preferred.

Formation of the diamidediol can be accomplished by combining at least about 2 moles of monoalkanolamine for every mole of diacid halide. Preferably, a slight excess (e.g., up to 10%) of monoalkanolamine is employed. The reaction is preferably conducted at ambient pressure and temperature in order to optimize the formation of the diamidediol and exclude or minimize the formation of product(s) other than the diamidediol. If desired, the reaction medium can be gently warmed to accelerate the rate of reaction, e.g., up to about 50° C., provided no significant quantity of undesirable product(s) are produced. The reaction is generally conducted within an inert organic solvent such as dimethyl formamide and an acid acceptor such as triethylamine which reacts with by-product HCl as the latter is produced forming a triethylammonium chloride precipitate.

The diamidediol is preferably recovered and purified prior to being used in the second step of the process, i.e., prior to the polymerization step which provides the polyesteramide. Known recovery and purification techniques can be used, e.g., passage through a column packed with silica gel.

The polymerization reaction can be accomplished by combining the diamidediol with an equimolar amount of a diacid halide which is either the same as or different from the diacid halide employed in the first step of the process. A suitable esterification catalyst such as $Sb_2O_3$ is added and the mixture is heated with stirring under dry nitrogen at temperatures of from about 150° to 250° C. for from about 10 to about 100 hours, and preferably at from about 175° to about 200° C. for from about 20 to about 40 hours, to provide the polyesteramide.

If desired, any portion of the diacid halide employed in the polymerization reaction, e.g., from about 1 to about 99 mole percent can be replaced with a like mole percentage of another difunctional reactant. Such difunctional reactants include two active groups selected from acid, amino, hydroxy or acid chloride groups. Preferably the difunctional reactant contains two of the same type of groups such as, for example, a diol, diamine, diacid or diacid halide.

The condensation polymerization of the diamidediol with the diacid halide results in the formation of the polyesteramide of this invention according to the reaction (shown for the particular case where the diamidediol and diacid halide are the only reactants and the diacid halide is the same as that used in the first step of the process):

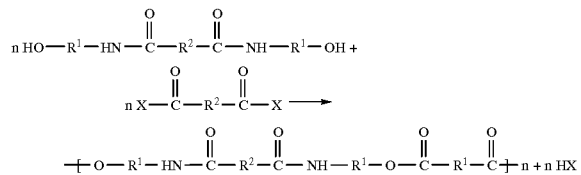

In this and the other polyesteramides herein, the average value of n can advantageously range from about 15 to about 100 and preferably from about 20 to about 60.

A preferred method of preparing the polyesteramide consists of dissolving the diamidediol in a solvent which is nonreactive with the acid halide and has a boiling point of 100° C. or higher, adding an acid acceptor such as the aforementioned triethanolamine, heating the mixture to reflux, rapidly adding an equimolar amount of diacid halide with vigorous mechanical mixing, separating the polyesteramide from the solvent and drying the polyesteramide at temperatures below its melting point. Suitable solvents include methylchloroacetate, chlorobenzene, 1,1,2-trichloroethane and 1,4-dioxane. The preferred solvent is chlorobenzene. This method has the advantage of not requiring the use of a catalyst, of yielding the polyesteramide in a relatively short period of time and producing high molecular weight polymer in a granular, easy-to-manipulate form. In addition, moisture which would otherwise react with the acidchloride can be readily excluded from the system by azeotropic distillation prior to addition of the diacidchloride. Polyesteramide prepared by this method can be further improved with respect to increasing its molecular weight by heating for several days under partial vacuum with a stream of dry nitrogen passing over the polymer at temperatures that are from about 10° to about 50° C. below the polymer melting temperature.

The polyesteramide herein is linear, exhibits good absorption properties and mechanical properties and is readily extruded into filaments and sheets and/or molded into various shapes employing known and conventional techniques. The polyesteramide can be formed into surgical articles using any know technique, such as, for example, extrusion, molding and/or solvent casting. The polyesteramide can be used alone or it can be blended with one or more other absorbable and/or nonabsorbable components. A wide variety of surgical articles can be manufactured from the polyesteramide described herein. These include, but are not limited to, clips and other fasteners, staples, sutures, pins, screws, prosthetic devices, wound dressings, drug delivery devices, anastomosis rings, and other implantable devices. Fibers made from the polyesteramide can be knitted or woven with other fibers, either absorbable or nonabsorbable, to form meshes or fabrics. Compositions including the polyesteramide can also be used as an absorbable coating for surgical devices.

Optional additives which may be present in compositions made from the polyesteramides described herein include plasticizers, release agents and other processing aids. Where the composition is used to make a surgical device, stearic acid or calcium stearate are particularly useful additives due to their biocompatibility.

In another aspect, compositions containing the polyesteramides described herein can be used to make reinforced composites. Thus, for example, the polyesteramide composition can form the matrix of the composite and can be reinforced with bioabsorbable or non-absorbable fibers or particles. Alternatively, a matrix of any bioabsorbable or non-bioabsorbable polymer composition can be reinforced with fibers or particulate material made from compositions containing the polyesteramides described herein.

In an alternative embodiment, the polyesteramide described herein is admixed with a filler. The filler can be in any particulate form, including granulate and staple fibers. While any known filler may be used, hydroxyapatite, tricalcium phosphate, bioglass or other bioceramics are the preferred fillers. Normally, from about 10 grams to about 400 grams of filler are mixed with 100 grams of polymer. The filled, cross-linked polymers are useful, for example, as a molding composition.

It is further contemplated that one or more medico-surgically useful substances can be incorporated into compositions containing the polyesteramide herein. Examples of such medico-surgically useful substances include, for example, those which accelerate or beneficially modify the healing process when particles are applied to a surgical repair site. So, for example, articles made from compositions containing the present polyesteramide can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the articles, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is also contemplated that it may be desirable to dye articles made from compositions containing the present polyesteramide in order to increase visibility of the article in the surgical field. Dyes, such as those known to be suitable for incorporation in sutures, can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, articles in accordance with this disclosure are dyed by adding up to about a few percent and preferably about 0.2% dye to the resin prior to extrusion.

It will be understood that various modifications may be made to the embodiments disclosed herein. Therefore the above description should not be construed as limiting, but merely as exemplifications of preferred embodiments. Those skilled in the art will envision other modifications within the scope and spirit of the claims appended hereto.

What is claimed is:

1. A polyesteramide comprising units of the structure

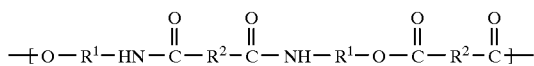

wherein $R^1$ and $R^2$ are divalent groups.

2. The polyesteramide of claim 1 comprising an average of from about 15 to about 100 of said units.

3. The polyesteramide of claim 1 comprising an average of from about 30 to about 60 of said units.

4. The polyesteramide of claim 1 wherein $R^1$ is a hydrocarbylene group of from 2 to about 20 carbon atoms.

5. The polyesteramide of claim 1 wherein $R^2$ is a hydrocarbylene group of from 2 to about 20 carbon atoms.

6. The polyesteramide of claim 4 wherein $R^2$ is a hydrocarbylene group of from 2 to about 20 carbon atoms.

7. The polyesteramide of claim 1 which comprising from about 15 to about 100 units of the structure:

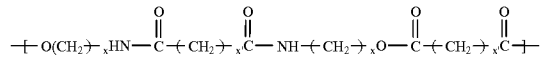

wherein x is from 2 to 4 and x' is from 2 to 4.

8. The polyesteramide of claim 7 wherein x is 2 and x' is 2.

9. A composition comprising the polyesteramide of claim 1 and at least one other absorbable polymer.

10. The composition of claim 9 wherein the other absorbable polymer is a polyester.

11. A composition comprising the polyesteramide of claim 1 and at least one other component selected from the group consisting of filler, medico-surgically useful substance and dye.

12. A process for making the polyesteramide of claim 1 which comprises reacting a monoalkanolamine with a diacid halide to provide a diamidediol and reacting the diamidediol with the same and/or different diacid halide under polymerization conditions to provide the polyesteramide.

13. The process of claim 12 wherein the monoalkanolamine has the structure $HO—R^1—NH_2$ in which $R^1$ is a hydrocarbylene group of from 2 to about 20 carbon atoms.

14. The process of claim 13 wherein $R^1$ is an alkylene group of from 2 to 4 carbon atoms.

15. The process of claim 12 wherein the diacid halide has possesses the structure

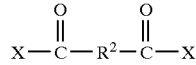

in which X is selected from the group consisting of F, Cl, Br and I and $R^2$ is a hydrocarbylene group of from 2 to about 24 carbon atoms.

16. The process of claim 15 wherein $R^2$ is an alkylene group of from 2 to 4 carbon atoms.

17. The process of claim 16 wherein $R^1$ is —$CH_2CH_2$— and $R^2$ is —$CH_2CH_2$—.

18. The process of claim 12 wherein the polymerization conditions include heating under reflux in an inert organic solvent.

19. The polyesteramide obtained by the process of claim 12.

20. An absorbable surgical device formed from the polyesteramide of claim 1.

21. An absorbable surgical device formed from the polyesteramide of claim 19.

* * * * *